(12) United States Patent
Fernandez

(10) Patent No.: US 10,235,906 B2
(45) Date of Patent: Mar. 19, 2019

(54) POST MORTEM RECONSTITUTION OF CIRCULATION

(71) Applicant: Maximum Fidelity Surgical Simulations LLC, Columbia, MO (US)

(72) Inventor: Joss Dean Fernandez, Columbia, MO (US)

(73) Assignee: Maximum Fidelity Surgical Simulations, LLC, Columbia, MO (US)

( * ) Notice: Subject to any disclaimer, the term of this patent is extended or adjusted under 35 U.S.C. 154(b) by 314 days.

(21) Appl. No.: 14/945,213

(22) Filed: Nov. 18, 2015

(65) Prior Publication Data

US 2016/0140878 A1 May 19, 2016

Related U.S. Application Data

(60) Provisional application No. 62/195,672, filed on Jul. 22, 2015, provisional application No. 62/157,654, (Continued)

(51) Int. Cl.
G09B 23/28 (2006.01)
G09B 23/30 (2006.01)
A01N 1/00 (2006.01)

(52) U.S. Cl.
CPC ............. *G09B 23/303* (2013.01); *A01N 1/00* (2013.01)

(58) Field of Classification Search
USPC ......... 434/262, 267, 268, 272, 295; 422/1, 3
See application file for complete search history.

(56) References Cited

U.S. PATENT DOCUMENTS 3,912,809 A * 10/1975 Rendon .................... A01N 1/00
27/22.2
4,982,481 A 1/1991 Deutscher
(Continued)

FOREIGN PATENT DOCUMENTS

WO 2006/124021 11/2006
WO 2007089777 8/2007
(Continued)

OTHER PUBLICATIONS

International Search Report and Written Opinion for Application No. PCT/US2015/061399 dated Feb. 2, 2016 (17 pages).
(Continued)

*Primary Examiner* — Kurt Fernstrom
(74) *Attorney, Agent, or Firm* — Brian L. Main; Kutak Rock LLP

(57) ABSTRACT

A system for reconstituting circulation in a cadaver includes at least a pump, a fluid driven by the pump, and operative fluid connections between the pump and the cadaver. The system may be used to occlude one or more arterioles within the cadaver. The system may include a first circuit that creates a first fluid path with vessels of the cadaver, with first circuit having a first fluid conduit, a heater unit, a first pump, and a resistance device. The system may also include a second circuit that creates a second fluid path with vessels of the cadaver that are different from the vessels of the first circuit, with the second circuit having a second fluid conduit and a second pump. Alternately, the system may include a first circuit that creates a first fluid path with vessels of the cadaver and a second flow path that creates a second fluid path with the reservoir, where the first circuit includes a first conduit, a second connector, a pump, a reservoir, and a connector.

25 Claims, 4 Drawing Sheets

Related U.S. Application Data filed on May 6, 2015, provisional application No. 62/081,462, filed on Nov. 18, 2014.

(56) References Cited

U.S. PATENT DOCUMENTS

| | | | |
|---|---|---|---|
| 5,178,620 A | | 1/1993 | Eggers et al. |
| 5,429,797 A | * | 7/1995 | Camiener ............... A01N 1/00 422/1 |
| 5,574,019 A | * | 11/1996 | Segall ..................... A01N 1/02 435/2 |
| 5,607,411 A | | 3/1997 | Heironimus et al. |
| 6,110,139 A | | 8/2000 | Loubser |
| 6,190,400 B1 | | 2/2001 | Van De Moer et al. |
| 6,191,193 B1 | | 2/2001 | Lee et al. |
| 6,218,099 B1 | | 4/2001 | Segall et al. |
| 6,312,694 B1 | * | 11/2001 | Thorpe ................ A61K 39/395 424/133.1 |
| 6,371,942 B1 | | 4/2002 | Schwartz et al. |
| 6,478,808 B2 | | 11/2002 | Nowakowski |
| 6,790,043 B2 | † | 9/2004 | Aboud |
| 6,824,389 B1 | * | 11/2004 | Garrett, Jr. ........... G09B 23/306 434/262 |
| 8,980,774 B2 | * | 3/2015 | Zhang ..................... C08L 33/02 264/171.1 |
| 9,968,292 B2 | * | 5/2018 | Gardner ................ A61B 5/4393 |
| 2002/0018752 A1 | * | 2/2002 | Krall ...................... A61K 31/05 424/9.4 |
| 2003/0180824 A1 | | 9/2003 | Mpock et al. |
| 2003/0186203 A1 | | 10/2003 | Aboud |
| 2003/0206884 A1 | * | 11/2003 | Barrow ................... A01N 1/00 424/75 |
| 2009/0012413 A1 | * | 1/2009 | Sabbah ............ A61B 17/12045 600/508 |
| 2009/0130104 A1 | * | 5/2009 | Muzykantov ...... C07K 16/2803 424/134.1 |
| 2010/0323339 A1 | | 12/2010 | Ritchie |
| 2012/0270197 A1 | * | 10/2012 | Brost ...................... G09B 23/30 434/267 |
| 2014/0270738 A1 | | 9/2014 | Lynch |
| 2016/0287744 A1 | * | 10/2016 | Kobayashi ............ A61L 31/047 |

FOREIGN PATENT DOCUMENTS

| | | |
|---|---|---|
| WO | 2011/126801 | 10/2011 |
| WO | 2014052158 A3 | 7/2015 |

OTHER PUBLICATIONS

Extended Search Report Issued by the European Patent Office for Application No. 15861329.9 dated May 4, 2018 (7 pages).
Aboud et al, Novel Simulation for training trauma surgeons,pp. 1484-1485, 2011, USA.†
Garrett, A human cadaveric circulation model, pp. 2001,USA.†
MedCure, press release, 2 pages, Oct. 2014, USA.†
Apreu, Robotic Transabdominal Control . . . Perfused-Cadaver Model, pp. 1177,1178. Oct. 2015.†
Morgan, Perfused Cadavers as a training model . . . , 2 pages, Nov. 2013, USA.†
Carey: Perfused fresh cadavers . . . , pp. 179,182,186, Mar. 2014, USA.†
Gray, plastinated veins of blue shark to . . . 2 pages, Apr. 2012, UK.†
Aboud New laboratory model for neurosurgical training pp. 1367,1368, Dec. 2002, USA.†
Rhoton Microsurgical anatomy of the distal anterior cerebral artery, pp. 204, 205. 1978, USA.†
Willaert, Postmortem Pump-Driven Reperfusion, pp. 17-18, Jan. 2014, switzrland.†
Wolff, Flap raising on pulsatile perfused cadaveric tissue, pp. 1423-1427, Apr. 8, 2014, Germany.†
Arbatli, Dynamic Human Cadaver Model for Testing, pp. 419, 420, 422. 2009, USA.†
Chevallier,Postmortem Circulation: A New Model for . . . , pp. 1-7, 2013, Europe.†
Carey,Simulation of plastic surgery and . . . , pp. e1-e7, 2013, USA.†
Russin, Simulation of a High-Flow Extracranial-Intracranial . . . , 7 pages, USA.†
Zapata M,Study of postmortem blood circulation. 1 page abstract, 1989, Spain.†

* cited by examiner
† cited by third party

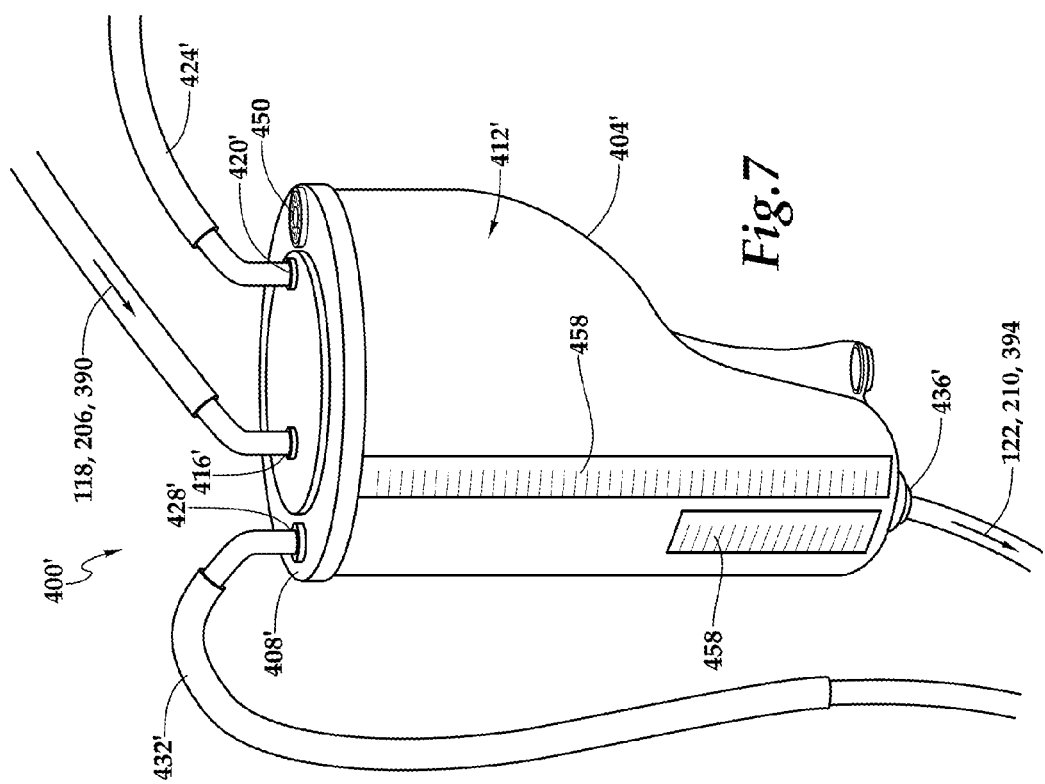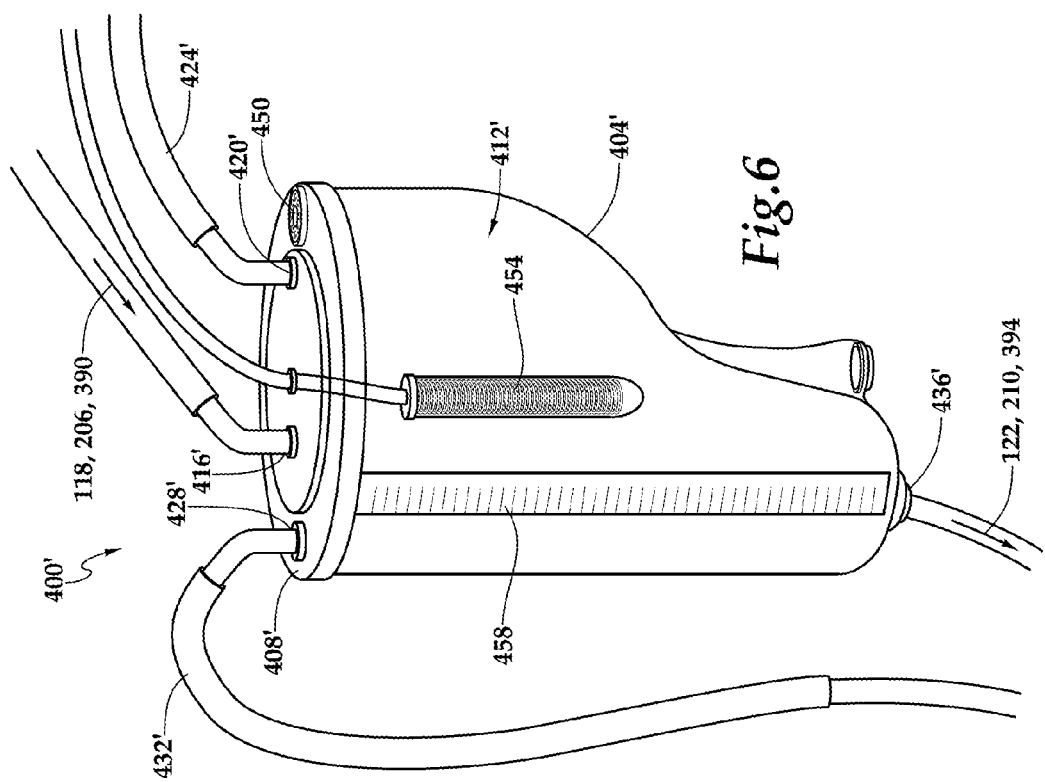

POST MORTEM RECONSTITUTION OF CIRCULATION

CROSS-REFERENCE TO RELATED APPLICATIONS

This application claims priority to U.S. Provisional Patent Application No. 62/081,462, filed on Nov. 18, 2014; U.S. Provisional Patent Application No. 62/157,654, filed on May 6, 2015; and U.S. Provisional Patent Application No. 62/195,672, filed on Jul. 22, 2015; the contents of each of which are fully incorporated herein by reference in their entireties.

TECHNICAL FIELD

The present disclosure relates generally to systems and methods for reconstituting circulation in a cadaver.

BACKGROUND

Currently, a model that appropriately approximates a live patient does not exist. Existing computer or synthetic simulations only approximate the anatomy and haptic feedback of a human or animal patient and thus, are poor substitutes for biologic tissues. In addition, animal models are insufficient because animal anatomy is not identical to human. Further, the use of animal models carries ethical issues. As a result, physician education as well as medical device development is stunted because practice on new techniques or with medical devices is difficult to complete. For example, across all specialties, physicians in training are facing a growing gap in procedural training. Furthermore, the public emphasis on surgical outcomes will place further strain on training programs. Studies have shown that resident participation in surgeries may be associated with an increase in complications, thus, leading to less resident participation in the name of improved outcomes, resulting in even further degradation of training. Similarly, increased regulatory scrutiny on medical devices is exposing the significance of a lack of a model that appropriately approximates a live patient.

BRIEF DESCRIPTION OF THE DRAWINGS

FIGS. 6 and 7 illustrate another reservoir usable with the circuits of FIGS. 1 and 2 and the system of FIG. 4.

DETAILED DESCRIPTION

Figure 1:
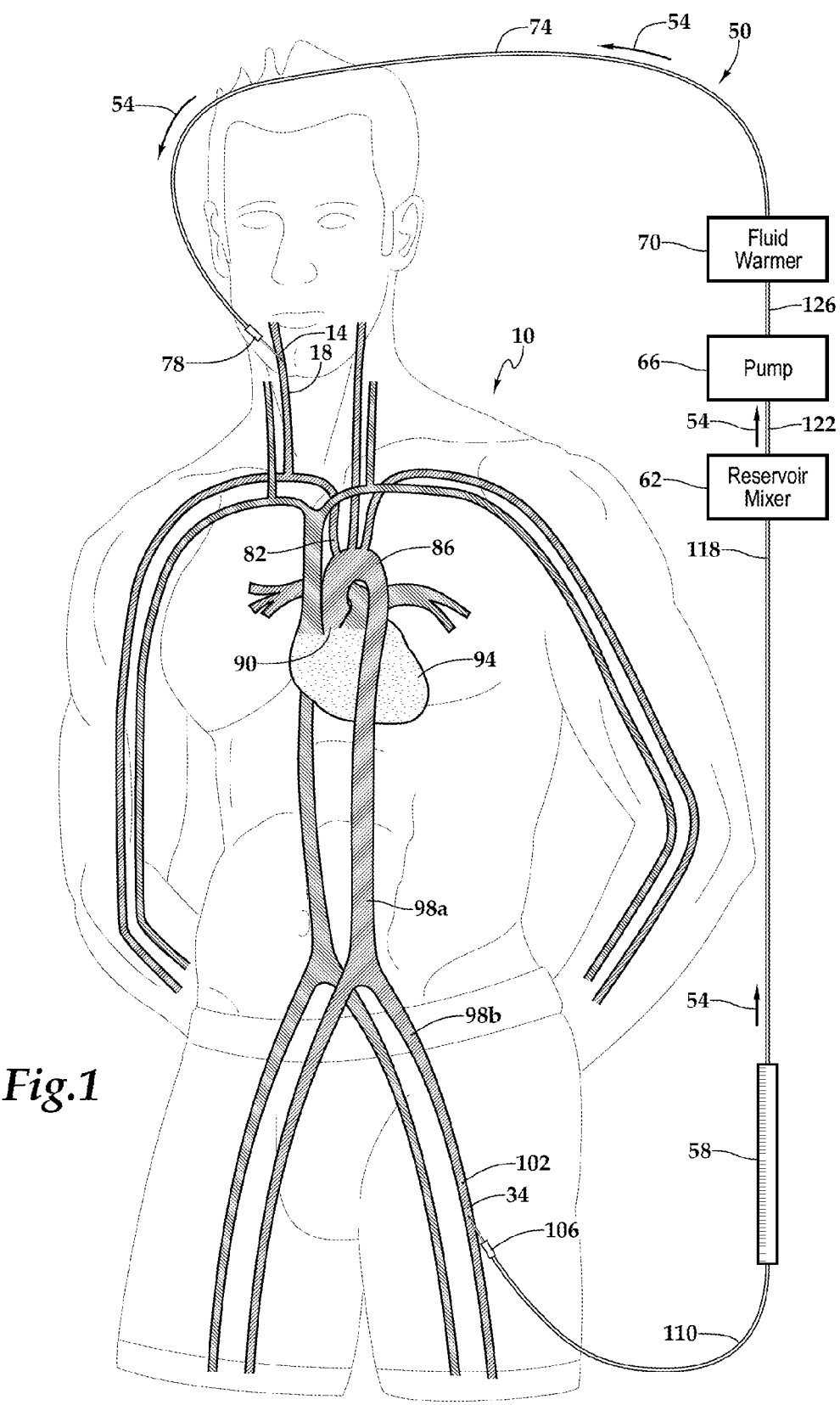
FIG. 1 illustrates a first circuit that reconstitutes arterial circulation in a cadaver.

Disclosed are systems and methods of reconstituting circulation in a human cadaver. Although only human cadavers are discussed and shown in detail herein, it should be understood that an animal cadaver could alternatively be used. A cadaver reconstituted with circulation according to the present disclosure can have life-like tissue integrity, anatomic accuracy, and a functional circulatory system to simulate bleeding. The disclosed systems and methods can thus provide an ideal model for physician training and medical device development.

The disclosed methods can include one or more of preserving a cadaver, perfusing the cadaver with a first fluid configured to occlude one or more arterioles of the cadaver, and perfusing the cadaver with a second fluid. The first fluid can be a perfusing mixture that includes a liquid medium, an embolization material, and a flocculating agent. It is to be understood that the perfusing mixture can be a homogeneous mixture (e.g., a solution), or a heterogeneous mixture (e.g., suspension, colloid). The second fluid can be blood (e.g., expired blood).

The disclosed methods can include one or more of preserving a cadaver, and perfusing the cadaver with a fluid configured to occlude one or more arterioles of the cadaver, where the fluid is configured to have blood-like physical properties. The disclosed methods can include reconstituting circulation in a cadaver by preserving the cadaver, perfusing the cadaver with a fluid configured to occlude one or more arterioles of a fluid pathway where the fluid is configured to have blood-like physical properties, and circulating the fluid through the fluid pathway to simulate circulation of blood therethrough.

The disclosed systems and methods can employ one or more heater units, pumps, or resistance devices.

The disclosed methods can include perfusing the cadaver with a fluid configured to occlude one or more arterioles of the cadaver where the fluid is configured to have blood-like physical properties. The disclosed methods can include reconstituting circulation in a cadaver by preserving the cadaver, perfusing the cadaver with a fluid configured to occlude one or more arterioles of a fluid pathway where the fluid is configured to have blood-like physical properties, and circulating the fluid through the fluid pathway to simulate circulation of blood therethrough.

The disclosed systems and methods provide several advantages. As one advantage, the methods of post mortem reconstitution of circulation can use whole body cadaver donors. Because the systems and methods can reconstitute circulation through the whole body cadaver, multiple portions of the cadaver can be used simultaneously or in sequence (e.g., to practice multiple medical procedures). As another advantage, the disclosed methods avoid the need to grossly ligate all branches of the system to be studied. For example, to study the aorta the branches to the arms and legs are ligated. This leaves a passive conduit to allow fluid to be perfused through one end of the aorta and egress out the other end. Unfortunately, there are many more branches to the aorta than just the extremities. Ligating all branches of the aorta is time consuming, technically demanding, and violates the integrity of the surgical model. As another advantage, the disclosed systems and methods allow use of cadavers without introducing offensive embalming fluid or freezing the cadavers, both of which can compromise the mechanical properties of the cadaver.

Figure 2:
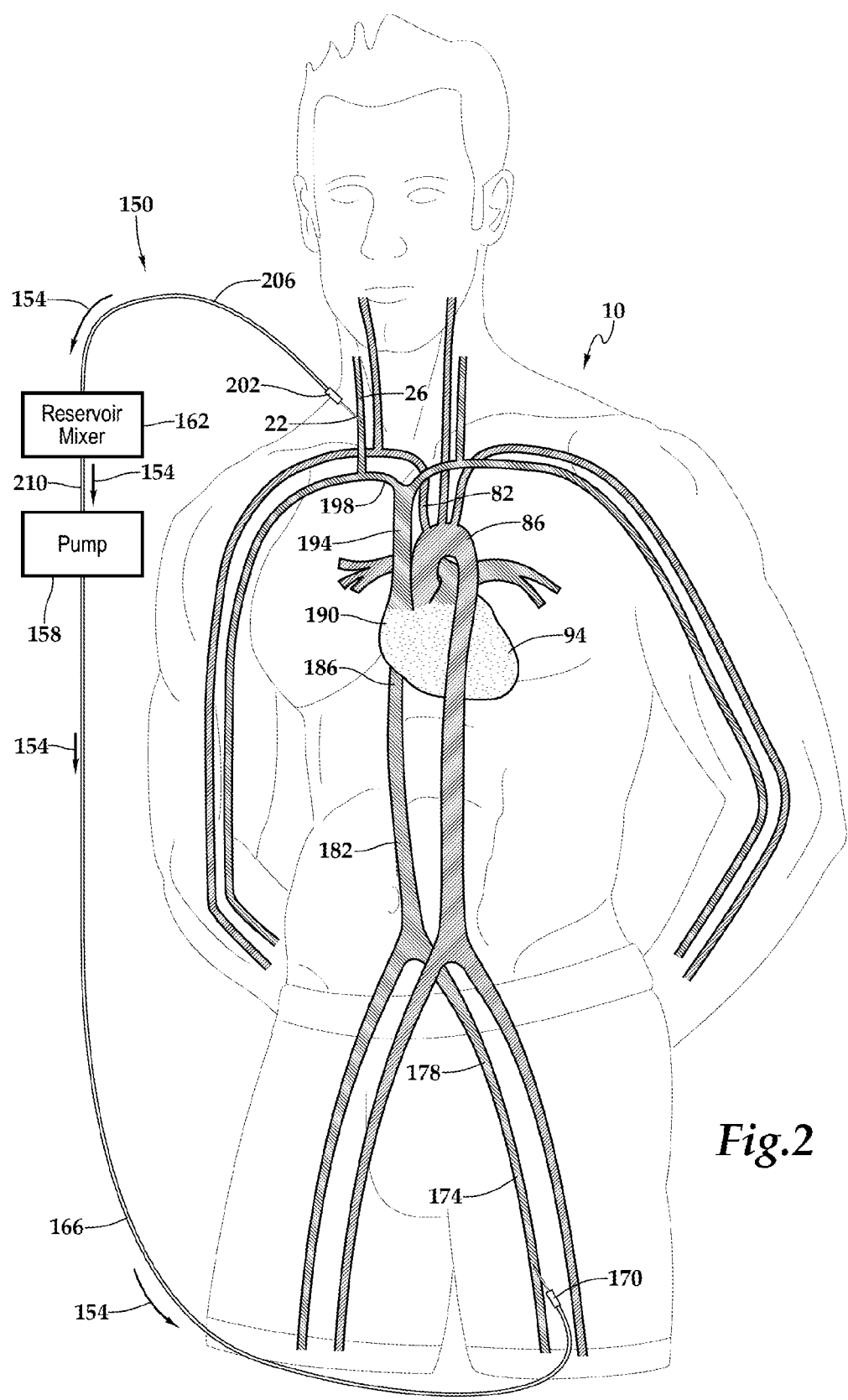
FIG. 2 illustrates a second circuit that reconstitutes venous circulation in a cadaver.
Figure 4:
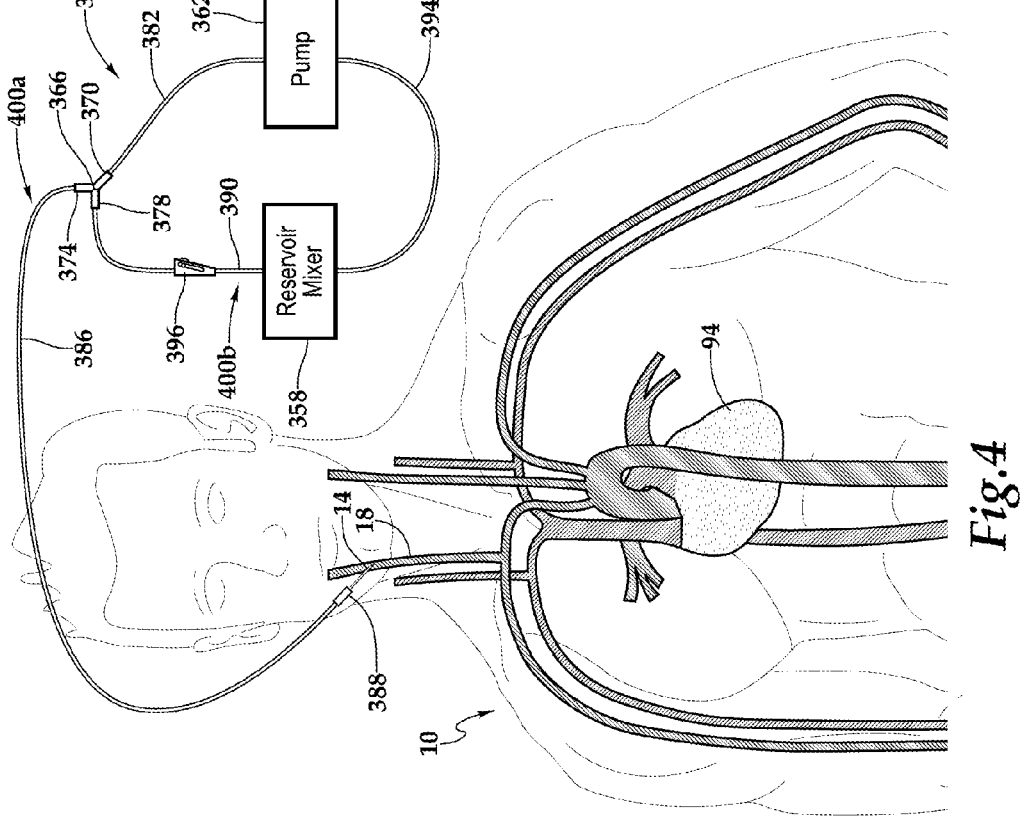
FIG. 4 illustrates a system that reconstitutes pulsatile arterial pressure in a cadaver.

FIGS. 1, 2, and 4 illustrate exemplary systems and methods according to the present disclosure.

Cadaver Preservation

Upon receipt of a whole body cadaver 10, preferably within 8 hours of expiration, the whole body cadaver 10 can be chemically preserved using an embalming solution. The whole body cadaver 10 can be chemically preserved by flushing the whole body cadaver to expel expired blood and injecting the embalming solution into the body. In particular, approximately 1 gallon of solution per 50-100 lb of body weight can be injected through an incision 14 created in the carotid artery 18. Preferably, approximately 1 gallon of solution per 75 lb of body weight is injected. The injected fluid can be pumped via a continuous pump (not shown), for example, through the circulatory system and exits or drains from the circulatory system through an incision 22 created in one or both of the internal jugular veins 26. In some embodiments, an auxiliary incision 34 is also made in the femoral artery 102 as well to ensure that all of the expired blood is removed from the whole body cadaver 10.

The embalming solution can be a solution including polyethylene glycol and dimethyl sulfoxide (DMSO). Antibacterial agents (e.g., zinc oxide powder) may be incorporated into the embalming solution. For example, about 0-20% by weight of zinc oxide powder may be incorporated; preferably at least 10% by weight. An exemplary embalming solution including DMSO is described in U.S. Pat. No. 5,679,333, the entire contents of which is incorporated herein by reference. DMSO has Food and Drug Administration (FDA) approval for use as a preservative of organs for transplant. The use of a polyethylene glycol and DMSO containing embalming solution can be used to preserve mechanical properties of the tissues, preferably such that the whole body cadaver 10 maintains lifelike properties. Additionally, once the whole body cadaver 10 is preserved, it can be stored at a temperature above 0° C., such as 10° C., for example, such that the whole body cadaver 10 can be used for up to two weeks with no noticeable decay.

Other attempts at post-mortem reconstitution of circulation use partially embalmed cadavers. Partial embalming is an embalming procedure in which a reduced concentration of offensive embalming solution such as formaldehyde or glutaraldehyde is used. Alternatively, fresh frozen cadavers are used for current post-mortem reconstitution of circulation. Both partial embalming and freezing techniques degrade tissue mechanics such that the cadavers lack lifelike properties. Therefore, in contrast to previous attempts at post mortem reconstitution of circulation, the disclosed method of post mortem reconstitution of circulation preferably uses whole body cadavers 10 that are kept fresh and stored at a temperature above 0° C., such as 10° C., for example.

Dual Circuit Cadaver System

Preserved cadavers can be prepared for use by integration into a dual circuit cadaver system. FIGS. 1 and 2 illustrate an exemplary dual circuit system according to the present disclosure. The system of FIGS. 1 and 2 includes a chemically preserved, whole body cadaver 10 in which two parallel circuits 50, 150 have been established. The first circuit 50 defines a first fluid path (illustrated by arrow 54) and including vessels of the whole body cadaver 10, a resistance device 58, a mixer reservoir 62, a first pump 66, and a heater unit 70. In particular, fluid passes through from the heater unit 70 through a first conduit 74 (e.g., tube) to a first cannula 78 placed in the carotid artery 18. In the illustrated embodiment, the heater unit 70 is a heat exchanger that warms the fluid to 37° C. Other types of heater units 70 may be used. The first cannula 78 is placed in the carotid artery 18 via the incision 14 that was made during the preservation process. The fluid is guided from the carotid artery 18 into the brachiocephalic artery 82 to the aorta 86. The aortic valve 90 prevents the fluid from going into the heart 94. Most of the fluid will flow down the descending aorta to the common iliac artery 98a to the external iliac artery 98b to the common femoral artery 102. The fluid exits the whole body cadaver 10 through a second cannula 106 in the femoral artery 102. The second cannula 106 is placed in the femoral artery 102 via the auxiliary incision 34 that was made during the preservation process. The second cannula 106 guides the fluid to the resistance device 58 by a second conduit 110. In the illustrated embodiment, the resistance device 58 is a cylindrical column that is elevated 20-50 cm above the level of the whole body cadaver 10 to create a pressure head. The pressure head of the first circuit 50 causes the behavior of the fluid to mimic that of flow during typical venous return. In other words, resistance device 58 provides the diastolic resistance in the circuit during pulsatile flow. The fluid then enters the mixer reservoir 62 via a third conduit 118. The mixer reservoir 62, among other functions, prevents an embolization material from precipitating. The mixer reservoir 62 is configured to continually mix the fluid contained therein. The first pump 66 sucks fluid from the mixer reservoir via a fourth conduit 122 and passes the fluid back to the heater unit 70 through a fifth conduit 126, where fluid is reintroduced to the whole body cadaver 10 to continuously follow the first fluid path 54. In the first circuit 50, the first cannula 78 is the arterial cannula and the second cannula 106 is the venous cannula.

The second circuit 150 as shown in FIG. 2 defines a second fluid path (illustrated by arrows 154) and including vessels of the whole body cadaver 10 that are different from the vessels of the first circuit 50, a second pump 158, and a reservoir 162. In particular, fluid is pumped by the second pump 158 through a sixth conduit 166 to a third cannula 170 that is inserted into the common femoral vein 174. From the common femoral vein 174, the fluid travels up the whole body cadaver 10 through the external iliac vein 178, the common iliac vein 182, and the inferior vena cava 186 before reaching the right atrium 190. Some fluid will pass through the heart 94 but will be obstructed by the pulmonary arteries which are occluded, which will be discussed below. The fluid goes from the right atrium 190 up the superior vena cava 194 through the brachiocephalic vein 198 into the internal jugular vein 26. The fluid exits the whole body cadaver 10 through a fourth cannula 202 inserted into the internal jugular vein 26. The fluid then passes through a seventh conduit 206 into the reservoir 162. From the reservoir 162, the fluid travels through an eighth conduit 210 and is collected by the second pump 158, and reintroduced to the whole body cadaver 10 to continuously follow the second fluid path 154. In the second circuit, the third cannula 170 is the arterial cannula and the fourth cannula 202 is the venous cannula.

In the illustrated embodiment, the conduits 74, 110, 118, 122, 126, 166, 206, 210 have a diameter between ⅜ and ½ inches. Conduits having other diameters may be alternatively used, however.

The first pump 66 can be a pulsatile pump. In a preferred set up, the input of fluid from a bottom of the mixer reservoir 62 enters the pulsatile pump 66 from the bottom and the outlet of fluid from the pulsatile pump 66 is from the top. Preferably, both the whole body cadaver 10 and the mixer reservoir 62 are positioned above the pulsatile pump 66. This orientation reduces kinking of the outlet conduit 126. Also, air is preferentially guided from the mixer reservoir 62 to the pulsatile pump 66 and prevented from being guided backward from the outlet conduit 126 to the pulsatile pump 66.

The pulsatile pump 66 simulates the pumping action of the heart 94. The pulsatile output closely simulates the ventricular action of the heart 94. This action emulates the physiological advantages of blood flow. Although, not shown the pulsatile pump 66 includes a power switch, a heart rate adjustment switch, a systole/diastole adjustment switch, and a stroke volume adjustment switch. The power switch selectively turns the pulsatile pump off and on. The heart rate adjustment switch determines simulated heart rate and should generally be set to between about 60-80 bpm although the heart rate can range from 35-150 bpm. The systole/diastole adjustment switch determines the amount of time the pump 66 spends in systole (e.g., pumping) and the amount of time the pump spends in diastole (e.g., not pumping). Preferably, the setting for systole/diastole should be set for between 40/60 and 35/65, although the setting for systole/diastole may be greater or less than the range give above. The stroke volume adjustment switch is a rotatable switch, for example, and determines the amount of fluid expelled from the pump with each pump. Preferably, the stroke volume for a dual access system (FIG. 1) should be set to expel between 30-40 cc per pump and the stroke volume for a single access system (FIG. 4), which will be described in greater detail below, should be set to expel between 20-30 cc per pump. The heart rate, systole/diastole, and stroke volume settings simulate the pumping action of the heart. To this end, blood pressure in the whole body cadaver can be adjusted if necessary. Accordingly, simulated blood pressure can be increased by increasing the amount of time the pump spends in systole (e.g., adjusting the systole/diastole setting) or by increasing the stroke volume (e.g., adjusting the stroke volume setting). Similarly, the simulated blood pressure can be decreased by decreasing the amount of time the pump spends in systole (e.g., adjusting the systole/diastole setting) or by decreasing the stroke volume (e.g., adjusting the stroke volume setting).

The second pump 158 can be a non-pulsatile pump (e.g., a centrifugal pump).

The first and the second fluid circuits can be configured to be operated simultaneously. In other words, arterial and venous perfusions can be performed simultaneously.

While the embodiment illustrated herein shows the first circuit 50 on the left side of the cadaver and the second circuit 150 on the right side of the cadaver, it should be understood that the circuits can be switched. In particular, the first circuit 50 can be implemented on the right side using the right carotid or auxiliary artery and the right common femoral artery. Similarly, the second circuit 150 can be implemented on the left side using the left internal jugular and left femoral veins.

Single Access Cadaver System

FIG. 4 illustrates another exemplary circuit. In particular, FIG. 4 illustrates an exemplary single access system 350 according to the present disclosure used on preserved cadavers. The system of FIG. 4 includes a chemically preserved, whole body cadaver 10 in which a fluid flow can be established. The system 350 includes vessels of the whole body cadaver 10, a reservoir or reservoir mixer 358, a pump 362, and a connector 366. Like the first pump 66 discussed above, the pump 362 is preferably a pulsatile pump. The connector 366 is a Y-connector and includes an inlet 370, a first outlet 374, and a second outlet 378. A first conduit 382 fluidly couples the pump 362 to the inlet 370. A second conduit 386 couples the first outlet 374 to a cannula 388 that is placed in the carotid artery 18 (although in other embodiments the cannula 388 may be placed in the femoral artery 102) via the incision 14 that was made during the preservation process. A third conduit 390 couples the second outlet 378 to the reservoir. A fourth conduit 394 fluidly couples the reservoir 358 to the pump 362. In the illustrated embodiment, the third conduit 390 includes a clamp 396 that changes the diameter thereof. In other embodiments, a clamp 396 may also be included on the second conduit 386.

Clamps can be included in suitable positions on one or more of the conduits in order to modulate the diameter of the conduits.

Upon actuation of the pump 362, fluid is drawn into the pump 362 from the reservoir 358 through the fourth conduit 394. The fluid drawn into the pump 362 is then ejected therefrom through the first conduit 382 to the connector 366. A portion of fluid is guided along a first fluid path 400a through the second conduit 386 on route to the whole body cadaver 10 and a portion of the fluid is guided along a second fluid path 400b through the through the third conduit 390 on route back to the reservoir. The clamp 396 on the third conduit 390 is configured to control the relative amount of the fluid in each respective fluid path, and also control the pressure of the fluid in each of the first and the second fluid paths 400a, 400b. For example, the user may leave the third conduit 390 completely unclamped. If completely unclamped, however, only half of the fluid will be guided to and flow through the whole body cadaver, which is not preferred for simulation purposes. In a more realistic example, the third conduit 390 is partially clamped such that a greater portion of the fluid flows through the first fluid path 400a than the second fluid path 400b. In this way, the user can control the amount of fluid flowing to the cadaver 10 to ensure a lifelike fluid flow and also to prevent the cadaver 10 from being overloaded with fluid (e.g., bursting a vessel because pressure of the fluid is too great). The fluid pumped to the cadaver 10 remains in the vessels, while the fluid guided to the reservoir is conserved to be recirculated, as discussed above. As the vessels of the cadaver 10 are filled with the fluid, the result is a pulsatile arterial system in the cadaver 10 but no significant flow within the cadaver 10 itself. This system is ideal for training for open surgical techniques. If an injury to a blood vessel is performed the vessel will bleed since puncture becomes the path of least resistance for the fluid to flow.

As discussed above, the circuits of the dual and single access circuit cadaver systems are merely exemplary. Accordingly, the user could create a circuit that directs fluid through any other suitable fluid pathway necessary to simulate a system or organ of the body during a desired procedure. Additionally, each cadaver is usable to simulate procedures on each system, organ, and circulatory path at least once. As discussed above, the cadaver can be uniquely embalmed and therefore is viable for at least two weeks for multiple procedures at different times.

In the illustrated embodiment, the conduits 382, 386, 390, and 394 have a diameter between ⅜ and ½ inches. Conduits having other diameters may be alternatively used, however. Similarly, the inlet and outlets 370, 374, 378 of the connector have a diameter between ⅜ and ½ inches. Connectors having other sizes and diameters may be alternatively used, however.

Vacuum/Suction Source

Figure 5:
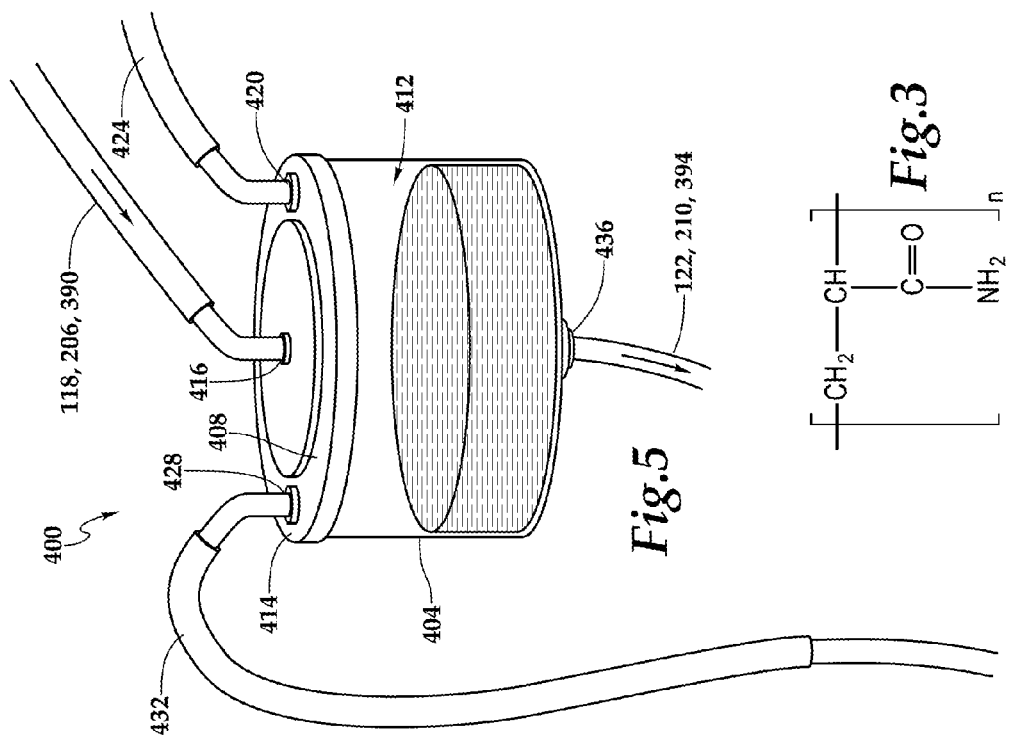
FIG. 5 illustrates a reservoir that is usable with the circuits of FIGS. 1 and 2 and the system of FIG. 4.

FIG. 5 illustrates reservoir 400 according to another embodiment. The reservoir 400 may be used in lieu of the mixer and reservoirs 62, 162, 358 of either the dual circuit system or the single access system discussed above. The reservoir 400 includes container 404 that is sealed by a lid 408 such that the container 404 defines an air-tight receptacle 412 having an air tight seal 414. The reservoir 400 also includes a first inlet 416 that is in fluid communication with the respective conduits 118, 206, 390 of each embodiment above, a second inlet 420 that is coupled to a suction vacuum source (not shown) via a tube or hose 424, and a third inlet 428 that is coupled to a tube or hose 432 and used as a suction source. The reservoir 400 also includes an outlet 436 in fluid communication with the respective conduits 122, 210, 394.

When in use, the vacuum source is applied to the reservoir 400 via the hose 424 to aid in draining the conduits 118, 206, 390. The tube 432 coupled to the reservoir 400 from the surgical field adjacent the cadaver 10 provides surgical suction, which is advantageous for suctioning or removing fluid from the field and returning it to the reservoir 400 thereby conserving fluid. In the case of major vessel trauma this will prevent from having to refill the reservoir 400 due to blood loss.

In another embodiment illustrated in FIG. 6, a reservoir 400' is illustrated that is similar to the reservoir 400 of FIG. 5; therefore like structure, will be indicated with a prime and only the differences discussed. In particular, the reservoir 400' may also include a purge valve 450 and an electrically powered electrical coil 454. The purge valve 450 prevents too much suction, while the electrical coil 454 is a heater that maintains the fluid at a selected temperature (e.g., about 37.5° C.). Furthermore, the reservoir 400' includes a measurement or volume indicator 458 that illustrates to the user how much fluid is contained within the reservoir 400'.

The reservoir of FIG. 6 may be, for example, Maquet's VHK 2000/2001 Venous Hardshell Cardiotomy Reservoir, although any other suitable reservoir may be used.

In another embodiment illustrated in FIG. 7, a reservoir 400' is illustrated that is similar to the reservoir 400' of FIG. 6. All similar structure is indicated with the same reference numerals. In this embodiment, the electrically powered electrical coil 454 is omitted, and a second measurement or volume indicator 458 is included.

The mixer and reservoirs 62, 162, 358, 400, 400' can be utilized in any of cadaver systems described herein. Also, any of the mixer and reservoirs 62, 162, 358, 400, 400' can include any combination of the structures and functionalities shown and described herein in connection with the any one mixer and reservoir 62, 162, 358, 400, 400'.

Cadaver Perfusion With A First Fluid

Living organisms rely on vascular endothelial permeability in the small arterioles and capillaries to ensure that blood and other fluids are not lost through the endothelium into the tissues. Vascular endothelial permeability is maintained by actively regulated apposition of adherens junctions (e.g., protein complexes that occur at cell-cell junctions in epithelial and endothelial tissues) and tight junctions (e.g., closely associated areas of two cells whose membranes join together forming a virtually impermeable barrier to fluid). The functions of the adherens junctions and the tight junctions are controlled by local mediators. Once the organism has expired, cellular respiration ceases due to lack of oxygen delivery to the cell wall. As a result the endothelial bonds that resist permeability within the capillaries of the circulatory system are no longer maintained. Attempts at introducing fluids through the circulatory system will result in losses through the endolethium into the tissues at the small arteriole and capillary levels. This leads to undesirable perfusion volume losses, loss of perfusion pressure, and distortion of tissue mechanics (e.g., bloating).

In an effort to avoid the undesirable effects described above and with renewed reference to FIGS. 1 and 2, the preserved whole body cadaver 10 is perfused using the dual, parallel circuits 50, 150 described above with a first fluid. In one embodiment, the first fluid is a perfusing mixture that includes an embolization material and a flocculating agent. The perfusing mixture is configured to occlude the small arterioles and the capillaries throughout the whole body cadaver 10 as it is circulated through the first and the second circuits 50, 150.

There is a drastic difference in surface area and diameter as the vascular tree branches from the largest blood vessel, the aorta, which is approximately 2 cm in diameter, to the smallest capillaries, which are approximately the size of erythrocytes (e.g., red blood cells) and therefore, approximately 6.2-8.2 microns. During surgical procedures clinically significant bleeding occurs at the 500 micron level. Therefore, the perfusing mixture can be configured to prevent flow of the perfusion fluid into any vessel having a diameter of less than the size of 500 microns. Exemplary particles include limestone dust (50-1000 microns), talcum powder (10 micron), polyvinyl alcohol (200-1000 micron), acrylic gelatin microspheres, or any combination thereof. In the illustrated embodiment, the embolization material is limestone powder.

Figure 3:
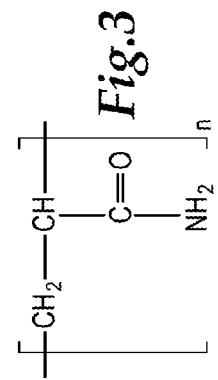
FIG. 3 illustrates the molecular structure of polyacrylamide.

The flocculating agent of the perfusing mixture promotes accumulation and coagulation of particles. In the illustrated embodiment, the flocculating is agent polyacrylamide, PAM (FIG. 3).

The embolization material and the flocculating agent are mixed with a liquid medium (e.g., water) in order to prepare the perfusing mixture.

Cadaver Perfusion With A Second Fluid

Once the small arterioles and capillaries have been occluded by the perfusion with the first fluid, a second fluid can be introduced into the cadaver using the first and the second circuits 50, 150 described above. In other words, after the initial use of perfusing mixture (e.g., approximately 1 gallon per 25-75 lbs of body weight and preferably 1 gallon per 50 lbs of body weight) there will be no more significant volume losses from within the reservoir and the option to switch to second fluid is available. The mixer reservoir 62 may be omitted when perfusing with the second fluid if the second fluid does not easily precipitate in solution. The second fluid may be expired blood, which approximates operating room conditions, or any other solution that mimics the flow properties of blood. Because the small arterioles and capillaries are occluded with the embolization material, the second fluid will circulate through each of the first and the second circuits while the first and the second pumps, respectively, are running.

While the second fluid is circulating, physicians, for example, can practice surgical techniques or test medical devices on the cadaver because the system is set-up to simulate life-like conditions during surgery on a live patient. These procedures may include endovascular procedures with fluoroscopy. Arteriograms and angiograms may be produced with this technique. Other surgical procedures include robotic, open vascular, cardiac, lung resections, endoscopy, otolaryngology, plastic surgery, renal transplant, orthopedic, and neurological procedures, although this list is not exhaustive. Because the cadaver is set-up like a live patient, incisions made into significant blood vessels will result in bleeding and loss of perfusion pressure.

Cadaver Perfusion And Simulation With A Single Fluid

In another embodiment, the preserved whole body cadaver 10 is perfused using the dual, parallel circuits 50, 150 described above, for example, with a single fluid that both occludes the small arterioles and capillaries and also exhibits blood-like properties to simulate life-like conditions during surgery on a live patient.

In particular, the single fluid used to perfuse the cadaver can include a mixture called "CF-1" and includes calcium carbonate or another embolization material with a range of 20-200 microns, a dispersant (e.g., a polyacrylate dispersant such as Accumer 1000), and a viscosifier (e.g., xanthan gum or other suitable polysaccharide). The dispersant can keep the pure calcium carbonate in suspension and the viscosifier (e.g., xanthan gum) can increase the viscosity of the single fluid, congeal the particles, and prevent water from traversing between (e.g., leaking through) the calcium carbonate particles. The single fluid can include a liquid medium, such as water. The single fluid can include one or more colorants. In some embodiments, the embolization material may include a range of 5 microns to 1,000 microns. In other embodiments, the embolization material may include a range of 10 microns to 500 microns. Still further, the embolization material may be prepared for use by passing the material through one or more 200 micron to 1000 micron filters. One possible formula of the CF-1 includes:

a) 1 cup of calcium carbonate per liter of fluid,
b) 10 ml of polyacrylate dispersant (Accumer 1000)/per liter of fluid,
c) ⅗ teaspoon of xanthan gum per liter of fluid,
d) a liquid medium (e.g., tap water), and
e) optionally a colorant that preferably has a washability similar to human blood and does not stain any type of tissue (e.g., 1½ table spoon of RED#40 per liter of fluid to create a red color, or a Chromatech Inc. Non-staining Polymeric Colorant that is either red or blue depending on the desired color).

In a preferred embodiment, the formula for CF-1 comes in a powder form that can be reconstituted in water (e.g., tap water). For example, CF-1 in powder form may include calcium carbonate, a dispersant (e.g., polyacrylate), a viscosifier (e.g, xanthan gum), and optionally a colorant. The powder can be economically prepared, shipped, and then reconstituted on site as needed.

The CF-1 formula does not affect x-ray and therefore, allows the use of intravascular devices under x-ray during the simulation (e.g., guide wires, stents, or the like). The single fluid having the CF-1 formula can occlude vessels below 200 microns (e.g., the capillary beds) such that volume losses are no more than 400 ml/hr.

In yet another embodiment, the single fluid may be a hydrocarbon (oil) based formula ("CF-E"), which uses hydrophobic forces to keep the fluid within the vasculature yet does not occlude the small vessels thereby still allowing fluid flow through branches of the vasculature. The hydrophobic proprieties also prevent the oil from entering the tissues. The hydrocarbon, hydrophobic formula may be an emulsion of oil in water for example. The oil emulsion can become unstable when in contact with capillary cell walls, which are made of phospholipids, and can in turn coat the endothelial (vessel lining) wall at the capillary level. Also, for the smaller size vessels (e.g., capillaries of ~10 microns in diameter) the emulsion having an appropriate size can coalesce and therefore obstruct correspondingly sized vessels. This may be the ideal solution for cadaver simulations that require the injection of contrast dye for visualizing the branches of the arterial tree for the introduction of medical devices. Using an oil emulsion in water instead of pure oil allows the use of aqueous contrast dyes. The emulsion is also ideal because it can have minimal to no effect on medical devices in an otherwise water-based formula. Like the CF-1 fluid discussed above, the CF-E fluid may include a colorant such as RED#40 or Chromatech Inc. Non-staining Polymeric Colorant (e.g., red or blue).

The CF-E may be an ethylene-vinyl acetate ("EVA") emulsion and may have one of several formulas. One formula for the CF-E includes xanthan gum (less than 1%), EVA polymer (about 27.8%), soy lecithin (about 1.7%), and water (about 72.2%). A second formula for the CF-E includes xanthan gum (less than 1%), EVA polymer (about 27.8%), acetylated lecithin (about 1.7%), and water (about 72.2%). A third formula for the CF-E includes xanthan gum (less than 1%), EVA polymer (about 27.8%), and water (about 72.2%). A fourth formula for the CF-E, similar to the first, second, and third formulas for the CF-E, includes approximately 10% and 28% EVA polymer, preferably approximately 15% with other material percentages varied accordingly. In the fourth formula, fluid losses are reduced to less than approximately 3 ml/s. In each of these formulas, water is the liquid medium although other suitable liquid mediums may be used instead. The lecithin and acetylated lecithin each act as a delivery agent to bind the EVA polymer to the membrane wall to occlude the small arterioles and capillaries and to prevent fluid retention by the tissues. The xanthan gum keeps the EVA emulsion stable.

Once the small arterioles and capillaries of the respective fluid pathway have been occluded by the perfusion with the CF-1 fluid or the CF-E fluid, the same can be continuously circulated throughout the fluid pathway of the cadaver (e.g., the first and the second circuits 50, 150 described above). Alternatively, after the initial use of the CF-1 fluid or the CF-E fluid, the option to switch to a second fluid is available as discussed above. Because the CF-1 fluid and the CF-E fluid can be used during the simulated procedures as well, both have physical properties that simulate the physical properties of blood circulating within a live body. Therefore, the CF-1 fluid and CF-E fluid both can have an average density of approximately 1060 kg/m$^3$, a viscosity of approximately 40/100 millipose, and be red (e.g., via the colorants discussed herein or another colorant). The CF-1 fluid and CF-E fluid can be configured to have a similar opacity and washability as blood circulating within a live body. The CF-1 fluid and CF-E can also be configured such that they do not stain or discolor any tissue (e.g., muscle, fat, nerve, blood vessel, etc.)

Discussed herein are several different fluids that can be circulated through a whole body cadaver to perfuse small arterioles and capillaries. Each can be used for any or all potential procedures simulated on the whole body cadaver. Furthermore, the different fluids may be chosen depending on the type of procedure being simulated. In other words, the first fluid and second fluid combination may be more appropriate for certain procedures, the CF-1 fluid may be more appropriate for certain procedures, and the CF-E fluid may be more appropriate for certain procedures. By way of a non-limiting example, CF-E may be more appropriate for angiograms because it does not entirely occlude the capillary bed, thereby allowing practitioners to observe a dye flowing through more branches of an arteriole under x-ray (e.g., in an angiogram). In another non-limiting example, CF-1 may be more appropriate for open surgical technique training because higher fluid pressures are achievable and the CF-1 fluid may be more predictable. Accordingly, any of the fluids discussed herein could be used for different procedures on the same whole body cadaver.

Materials

The pump hardware may include: Harvard Apparatus Pulsatile Pump Item #553305 Model 1423 Harvard Apparatus Pulsatile Blood Pump for Large Animals, Hemodynamic Studies, Harvard Apparatus Pump tubing 75-0461 is the 9/16" ID Tygon ND100-65 tubing, Harvard Apparatus Centrifugal Pump 732470 BVP-ZX Centrifugal Pump, 230 VAC, and/or Harvard Apparatus Centrifugal Pump Head and tubing.

The reservoirs may include a Medtronic Intersept Cardiotomy Reservoirs.

The agitator may include a handheld agitator mixer.

The heater unit may include any type of Suns Dual Heater Cooler Model #11160 and/or a Medtronic ECMOtherm II Heat Exchanger.

The tubing and connectors may include 9/16 inch, 1/2 inch, or 3/8 inch tubing, and appropriate associated connectors, convertors, and adaptors.

The surgical equipment may include a blade scalpel (e.g., #15 and/or #11), scissors (e.g., one or both of Metzenbaum or Mayo scissors), hemostats, needle drivers (e.g., 7 in), Prolene 5-0 on RB needle, Prolene 4-0 on SH needle, 16 F red rubber catheters, Rommel Tourniquet, 2-0 silk ties, 2-0 silk suture on SH needle, and tubing clamps.

Additional materials such as an IV pole and duct tape may also be used.

The materials and devices listed herein are merely exemplary and other or additional materials and devices may be used.

First Example

As discussed in detail above, the flocculating agent (e.g., PAM) promotes aggregation of particles embolization small blood vessels. The effects of perfusion volume losses were examined using isolated pig hearts. Water alternating with limestone powder with flocculant was introduced into isolated pig hearts through the left coronary artery using a coronary ostial cannulae. The distal left anterior descending artery was cannulated using a 5 french sheath to allow egress of fluid. A total of 60 ml of solution was introduced each time. The collected volume of egress was compared between water, limestone powder flocculant solution (floc) and repeated with water after a heart was treated with the limestone powder flocculant solution. The following table demonstrates the effects of using a limestone flocculant solution to prevent volume losses by embolizing capillaries.

|  | Heart 1 | Heart 2 | Heart 3 | Heart 4 |
| --- | --- | --- | --- | --- |
| Water | 23 ml | 20 ml | 19 ml | 30 ml |
| Floc | 12 ml | 6 ml | 8 ml | 20 ml |
| Water after Floc | 10 ml | 11 ml | 10 ml | 28 ml |

The table above indicates the volume loss with different types of perfusion fluid in pig hearts. A total of 60 ml was injected each time. 5 ml was assumed to be left within the circuit and not counted as loss.

Unfortunately, the manner in which the pig hearts were harvested resulted in cut edges which produced excess losses especially in heart 4. Nevertheless, the ability for the limestone flocculant solution to embolize the capillary bed and prevent tissue edema was demonstrated.

Second Example

As discussed in greater detail above, a single fluid (e.g., CF-1 or CF-E) may be used to perfuse the cadaver. The relationship between concentrations of EVA polymer within CF-E fluid, fluid losses, and achievable pressures were tested in a whole human cadaver using the dual circuit cadaver system described above. Additionally, the CF-E with varying concentrations of EVA polymer as well as CF-1 were observed within blood vessels in an angiogram to determine the level or degree of branching that is visible. All data was gathered at a rate of 40 bpm, a stroke volume of 15 ml, and 25% systole within a 200 kg, 68 year old male cadaver that was 2 weeks postmortem. The left carotid artery was used for inflow via an 18f cannula, and the left femoral artery was used for outflow via an 18f cannula.

| Fluid | Maximum Pressure Achieved | Fluid Loss Rate | Branching Visible |
| --- | --- | --- | --- |
| 1% EVA polymer CF-E | 30 mmHg | 20 ml/s | All branches visible |
| 5% EVA polymer CF-E | 45 mmHg | 7 ml/s | All branches visible |
| 8% EVA polymer CF-E | 59 mmHg | 5 ml/s | $3^{rd}$ Degree Branches visible |
| 10% EVA polymer CF-E | 68 mmHg | 3.8 ml/s | $2^{nd}$ Degree Branches visible |
| CF-1 | >80 mmHg | <1 ml/s | No branching visible |

The table above indicates that the maximum pressure achievable with the CF-E fluids of varied EVA polymer concentration increases as EVA polymer concentration increases. The fluid loss rate is also inversely related to EVA polymer concentration. Finally, the branching that is visible reduces as the EVA polymer concentration increases. An advantage of each of the CF-E fluids described in the table is the ability to conduct angiograms due to the visibility of arterial branching when using these fluids. Additionally, it is clear CF-1 is a good fluid for use, for example, in open surgical operation simulation due to the higher maximum pressures that are achievable. However, one limitation of CF-1 is the lack of visible branching in an angiogram. This is due to the occlusions caused by embolic particles, which prevent fluid flow through secondary and tertiary arterial branches thereby blocking dye used in an angiogram from penetrating these branches. Accordingly, the branches are not visible under x-ray (e.g., in an angiogram).

It is to be understood that the present disclosure is not limited in its application to the details of construction and the arrangement of components set forth in the description or illustrated in the following drawings. The invention is capable of other embodiments and of being practiced or of being carried out in various ways.

Various features and advantages of the invention are set forth in the following claims.

What is claimed is:

1. A method of occluding one or more arterioles, venules, or capillaries in a cadaver, the method comprising:
   perfusing the cadaver with a fluid configured to occlude one or more arterioles, venules, or capillaries of the cadaver, and
   wherein perfusing the cadaver with a fluid includes perfusing the cadaver via a single point of fluid communication with the cadaver.

2. The method of claim 1, wherein the fluid includes a liquid medium, a solid embolization material, a dispersant, and a viscosifier.

3. The method of claim 2, wherein the liquid medium includes water.

4. The method of claim 2, wherein the embolization material has an average particle size ranging from 5 microns to 1,000 microns.

5. The method of claim 2, wherein the solid embolization material is limestone dust or powder, talcum powder, acrylic gelatin microspheres, calcium carbonate, or a combination thereof.

6. The method of claim 2, wherein the solid embolization material is prepared for use by passing the material through one or more 250 micron to 1000 micron filters.

7. The method of claim 2, wherein the viscosifier is xanthan gum.

8. The method of claim 1, wherein the fluid is configured to occlude one or more arterioles, venules, or capillaries that have a diameter that is less than or equal to 500 microns.

9. The method of claim 1, wherein the fluid is a solid suspension.

10. The method of claim 1, wherein the embolization material has an average particle size ranging from 10 microns to 500 microns.

11. A method of reconstituting circulation in a cadaver having a vasculature, the method comprising:
perfusing at least a portion of the vasculature of the cadaver with a fluid via a single access point of the vasculature; and
pulsing the fluid within the vasculature.

12. The method of claim 11, wherein the fluid includes a liquid medium, a dispersant, a solid embolization material, and a viscosifier.

13. The method claim 12, wherein the solid embolization material is limestone dust or powder, talcum powder, acrylic gelatin microspheres, calcium carbonate, or a combination thereof.

14. The method of claim 12, wherein the viscosifier is xanthan gum.

15. The method of claim 12, wherein the liquid medium includes water.

16. The method of claim 11, wherein the pulsing comprises pumping a first portion of the fluid into a first fluid path including at least a portion of the vasculature, and pumping a second portion of the fluid into a second fluid path including a reservoir outside the vasculature.

17. The method of claim 16, wherein pumping a second portion of the fluid through a second fluid path includes recirculating the fluid.

18. A method of reconstituting circulation in a cadaver having a vasculature using a system including a pump having an inlet and an outlet, and a reservoir, the method comprising:
providing a first fluid path in fluid communication with the outlet of the pump and including at least a portion of the vasculature;
providing a second fluid path in fluid communication with the outlet of the pump and including the reservoir containing a volume of fluid therein;
pumping a first portion of the fluid into the first fluid path;
pumping a second portion of the fluid into the second fluid path.

19. The method of claim 18, wherein the fluid is configured to occlude one or more arterioles, venules, and capillaries of the vasculature.

20. The method of claim 19, wherein the fluid is configured to non-surgically occlude one or more arterioles, venules, and capillaries of the vasculature.

21. The method of claim 18, wherein the second fluid path is in fluid communication with the inlet of the pump.

22. The method of claim 18, wherein the first fluid path and the second fluid path are in fluid communication.

23. The method of claim 18, further comprising adjusting the relative amount of the fluid in the first fluid path and the second fluid path by at least partially restricting the flow of fluid through the second fluid path.

24. The method of claim 23, wherein restricting the flow of fluid through the second fluid path includes using a clamp.

25. A method of occluding one or more arterioles, venules, or capillaries in a cadaver, the method comprising:
perfusing the cadaver with a fluid configured to occlude one or more arterioles, venules, or capillaries of the cadaver, and
wherein the perfusing the cadaver with a fluid includes perfusing the cadaver without a point of egress.

* * * * *